(12) United States Patent
Braunston

(10) Patent No.: US 10,007,987 B1
(45) Date of Patent: Jun. 26, 2018

(54) ENHANCED TOOTH SHADE MATCHING SYSTEM

(71) Applicant: Dennis Braunston, Issaquah, WA (US)

(72) Inventor: Dennis Braunston, Issaquah, WA (US)

(*) Notice: Subject to any disclaimer, the term of this patent is extended or adjusted under 35 U.S.C. 154(b) by 222 days.

(21) Appl. No.: 15/015,429

(22) Filed: Feb. 4, 2016

(51) Int. Cl.
*G06K 9/00* (2006.01)
*G06T 7/00* (2017.01)
*G06K 9/62* (2006.01)
*H04N 1/60* (2006.01)

(52) U.S. Cl.
CPC .......... *G06T 7/0014* (2013.01); *G06K 9/6202* (2013.01); *G06T 7/0081* (2013.01); *H04N 1/60* (2013.01); *G06T 2207/30036* (2013.01)

(58) Field of Classification Search
None
See application file for complete search history.

(56) References Cited

U.S. PATENT DOCUMENTS

| | | | |
|---|---|---|---|
| 5,177,694 A | 1/1993 | Graham | |
| 5,371,615 A | 12/1994 | Eschbach | |
| 5,823,778 A * | 10/1998 | Schmitt | A61C 9/00 433/214 |
| 6,190,170 B1 * | 2/2001 | Morris | A61C 19/10 433/203.1 |
| 6,328,567 B1 * | 12/2001 | Morris | A61C 19/10 433/203.1 |
| 6,331,113 B1 | 12/2001 | Morris | |
| 6,793,489 B2 | 9/2004 | Morris | |
| 7,563,095 B2 | 7/2009 | Morris | |
| 8,848,991 B2 * | 9/2014 | Tjioe | G01J 3/0264 382/128 |
| 8,998,613 B2 | 4/2015 | Jung | |
| 9,008,417 B2 | 4/2015 | Rohner | |
| 9,014,440 B2 * | 4/2015 | Arumugam | A61B 6/14 378/62 |
| 9,060,832 B2 * | 6/2015 | Karim | A61C 13/0009 |
| 9,183,641 B2 | 11/2015 | Mauer | |
| 9,449,026 B2 * | 9/2016 | Wang | G06F 17/30277 |
| 9,717,417 B2 * | 8/2017 | DiMaio | A61B 5/0075 |
| 2005/0283065 A1 * | 12/2005 | Babayoff | A61B 1/00009 600/407 |
| 2008/0212899 A1 * | 9/2008 | Gokturk | G06F 17/30259 382/305 |
| 2010/0233655 A1 * | 9/2010 | Karim | A61C 13/0009 433/172 |
| 2011/0110574 A1 * | 5/2011 | Banumathi | A61B 6/14 382/132 |
| 2013/0266217 A1 * | 10/2013 | Gershon | G06F 17/3025 382/164 |

* cited by examiner

Primary Examiner — Tahmina Ansari
(74) Attorney, Agent, or Firm — Bert P. Krages, II

(57) ABSTRACT

A system for the color matching of dental restorations with teeth using a high degree of color correction followed by a display of maps showing the distribution of shades and values over the face of a tooth. The system can further utilize filters to output shade maps consisting of a predetermined number of shades and allow a technician to perform a virtual try in of the restoration in the patient's mouth.

19 Claims, 8 Drawing Sheets

ENHANCED TOOTH SHADE MATCHING SYSTEM

BACKGROUND OF THE INVENTION

An important aspect of dental restorations is the accurate shade matching of the shade of the restoration work to the natural teeth of a patient. Such matching can be difficult because natural teeth often have different optical properties than restorative materials. In particular, teeth exhibit the properties of translucency, opalescence, and fluorescence whereas restorative materials, such as dental porcelain, react to light differently depending on the underlying material such as zirconia, lithium disilicate, porcelain fused to metal or pressed ceramics are generally opaque and do not transmit light although they reflect and absorb it. Thus, matching an artificial restoration to natural teeth is as much art as it is science, encompassing a combination of clinical skill, experience, shade matching systems, and lighting conditions.

The traditional method for shade matching consists of visually comparing a shade tab to a tooth. Such shade tabs are fundamental tools used to communicate information in order to match color in the manufacture of prosthetic teeth, crowns, inlays, and similar products. The selection of a match, when using shade tabs, is a subjective choice done by eye. The information is written down on a lab form and communicated to the lab ceramist. Sometimes a picture of the tooth with the shade tab is made and also communicated. Opportunities for inaccuracies are inherent when conducting visual comparisons using shade tabs. Examples of sources that cause inaccuracies are eye fatigue, improper lighting, genetics and similarities among shade tabs. Also, once manufactured, there is no good way, other than a try-in with the patient, to determine if the restorative work will match. This is not only frustrating, but also a waste of time and money for the doctor, patient, and dental laboratory. Even when a tooth does not match, the corrective factor is not always easily determined.

Ideally, the clinician will convey the primary tooth shade characteristics of hue, chroma, and value to the technician, so that he or she may match the work to the remaining teeth. Hue refers to the wavelength of observed radiant energy, chroma describes the saturation of the hue, and value describes a color's relative darkness. Value is often the most important dimension of shade because it is noticeable if this parameter is off by just a small amount.

A photograph of the tooth adjacent to a shade tab can provide useful information to a technician. Editing software can be used to compensate for the color errors in digital photographs by conducting a color transformation in accordance with color references. Such references can contain the shade tabs of a shade system along with black, white, and gray. Although editing software can transform the depiction of color in a photographic image, corrected photographs do not always enable a technician to achieve a suitable match because natural teeth and restorative materials have different optical properties, and information such as the tooth shades, translucency and value are not revealed. What is needed is a method of transforming photographs that provides technicians with more information about the teeth to be matched than a digital photograph that has been nominally corrected for color.

SUMMARY OF THE INVENTION

The invention comprises a computer, which can be connected to a web based, secure, encrypted remote server that processes digital images. It optimizes an image in a number of different ways, so that a technician or dentist can glean information about the visual appearance of a tooth in order to fabricate an artificial restoration. Another use would be for patients to see more clearly the degree of teeth bleaching, in-house milling of teeth by a dentist, or the act of direct composite bonding not needing the services of a dental laboratory.

The system provides a more accurate and meaningful level of color correction based on a combination of black, white, and gray points in addition to at least two tooth-like, porcelain references in the form of shade tabs. Color correction, based on this combination, better reveals the shade of tooth colored objects, than just using black, white and a single shade tab. This combination, increases contrast so that information is more discernable than images that are corrected based on black, white and gray points alone. It also fixes excessive brightening or darkening of the image along with loss of detail. The resulting image is more useful to a technician or dentist because it more realistically depicts how a tooth appears and reveals more information than standard images in the context of its setting in a mouth or prosthetics on a work bench.

In addition, the inclusion of the shade tab references overcomes a problem inherent in corrections based on black, white, and gray points alone. Although such corrections can produce accurate neutrals (i.e., achromatic colors), they do not always produce accurate representations of the chromatic colors. The present invention largely overcomes this problem.

The system also can determine a gray scale value on a portion of the tooth. This provides useful information on which a technician can base a restoration. The gray scale value can be output in terms of a shade tab reference value, which some technicians prefer to use as a starting point on which to manufacture a restoration.

Another aspect of the system is that it can create maps of shade and translucency values which can be segmented so that only a specific number of discrete shades are displayed. For example, a shade map may be displayed showing two, three, four. or all shades depending on whether the restoration will be seen, as in the front of the mouth, or not seen as easily, as in the back.

The ability to specify the number of shades shown in a map allows the technician to rapidly analyze the tooth and make informed decisions on how to select colors for the restoration. Too many shades or unwanted highlights are not always useful because they cannot be reproduced and frequently hide information that is useful.

Another useful feature of the system, is its ability to provide a library of shade guides and modifiers that instantly translates from one to another. A dentist may insert in the shade reference a given shade tab of a shade guide from a particular brand of porcelain but the lab technician may use a differing brand or even mix brands. This is a problem. For example, the dentist inserts in the shade reference a Vita Classic D3 shade tab, made from VITA™ porcelain but the technician prefers another manufacturer's porcelain such as CHROMASCOPE™, whose nomenclature or shade with the same name look different. A translation from one to another is needed because existing translations are not always accurate, known or easily found. With this invention, anything in the picture can be translated as long as it is in the systems library. This includes more obscure things such as stump shades (a prepped tooth) and gum tissue. Modifiers are used for blending more unusual tooth colors and are often a part of the shade guide system. These are often extremely difficult for technicians to determine by eye. The system can mathematically determine any of these shades instantly.

An additional problem occurs with the use of translucent restorative materials when using traditional shade guides. This is because the underlying value, whether a stump or implant, are often times very dark, and affects the final outcome. For example, say the target shade is an A1 shade and the stump is dark. There is currently no mechanism to determine or tell the technician what shade of restorative material to use to get to the A1 shade. Should they choose A1, the outcome from translucent material will probably be too dark. The invention includes a correction value that calculates for material translucency and thickness and provides the correct choice of material.

One longstanding problem with matching restorations with natural teeth is that the visual environment surrounding the tooth can adversely affect accurate perception. The system addresses this problem by allowing the technician to isolate the tooth within an image and replace the background with one that is a solid neutral. This enables the technician to view the tooth in isolation to eliminate the effects of optical illusions on perception. The backgrounds may be modified to consist of a specific color and value.

Quality control is a critical and multifaceted part of the system. Another means of permitting the user to evaluate the quality of the restoration, is to virtually fit the restoration into the mouth. This is made possible by the high degree of color correction. To perform a virtual try-in, the technician ensures that the color corrected image of the mouth is loaded into a window and then a color corrected image of the restoration is loaded into another window. The technician can then drag and drop the restoration from its window over to the other window and evaluate how well it appears in the mouth. A virtual try-in can also be saved as a new image to forward to the treating dentist or patient for input or approval.

In addition to the restoration, the system can also allow a technician to perform a virtual try in using a representation of shade tab instead of the restoration. As with the virtual try in using the restoration, the technician can create a new image depicting a shade tab located in the mouth. By comparing an image of virtual try ins of a restoration with an image of a virtual try in of a shade tab, the technician will be able to detect subtle discrepancies in value or translucency effects that can sometimes detract from a restoration that otherwise is correct with respect to hue and chroma.

Consistent photography is an important aspect of the invention. The use of a telescoping, adjustable, distance making device that locks in the camera and shade references consistently produces the correct kind of images. This greatly reduces the creation of non-standard images that are not at the correct angle or are otherwise unusable. The device also is adjustable in length, height and width to accommodate most commercial cameras. An optional lighting system can be used which is important because many cameras do not provide even lighting at the optimal correct angle. The balanced, diffused lighting at the optimal angle makes for a better standardized image and eliminates an image with too many highlights or glare in the wrong places.

DETAILED DESCRIPTION OF THE PREFERRED EMBODIMENT

Figure 1:
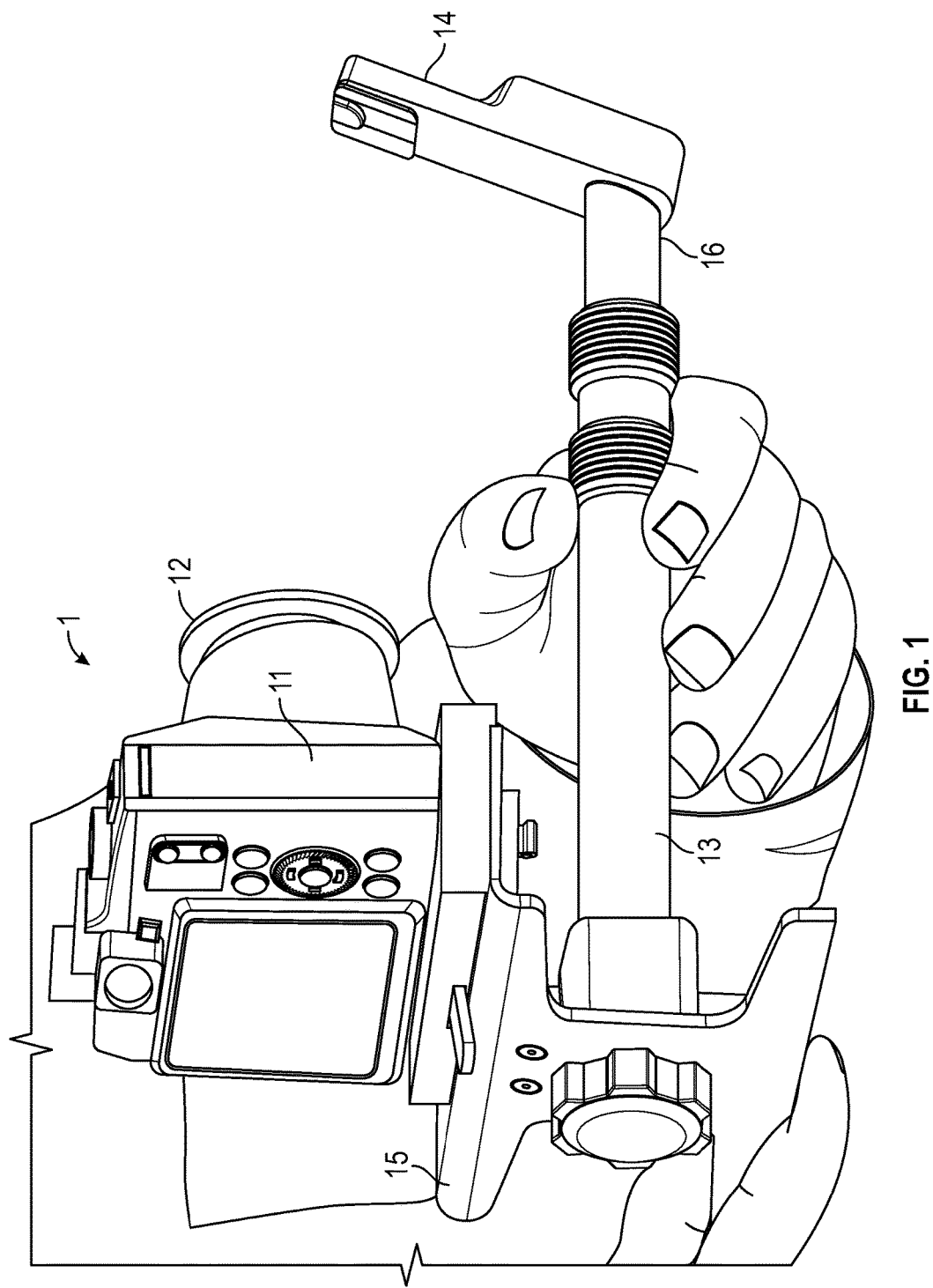
FIG. 1 is a drawing depicting the extension arm and camera for photographing a patient's mouth.

The first step is to create a digital camera image of the patient's tooth that depicts the tooth adjacent to a reference target. As shown in FIG. 1, the preferred assembly 1 for taking the images comprises a digital camera 11 with a ring flash 12 that is mounted on an adjustable extension arm 13 that supports the camera 11 at the proximal end 15 and supports a reference target 14 at the distal end 16. The purpose of the extension arm 13 is to provide precision, consistency and predictability in taking digital images for shade determination. By holding the reference target 14 at a constant distance and angle from the camera 11, the extension arm 13 maintains a consistent position and lighting of the tooth relative to the camera 11 and ring flash 12. However, it is not essential to the invention that such an assembly 1 be used. In addition, means of illumination other than a ring flash 12 may be used. Examples include twin flashes, camera mounted flash, and off camera lights. It is preferred that the color temperature of the light be within the range of 5000-6000K.

Figure 2:
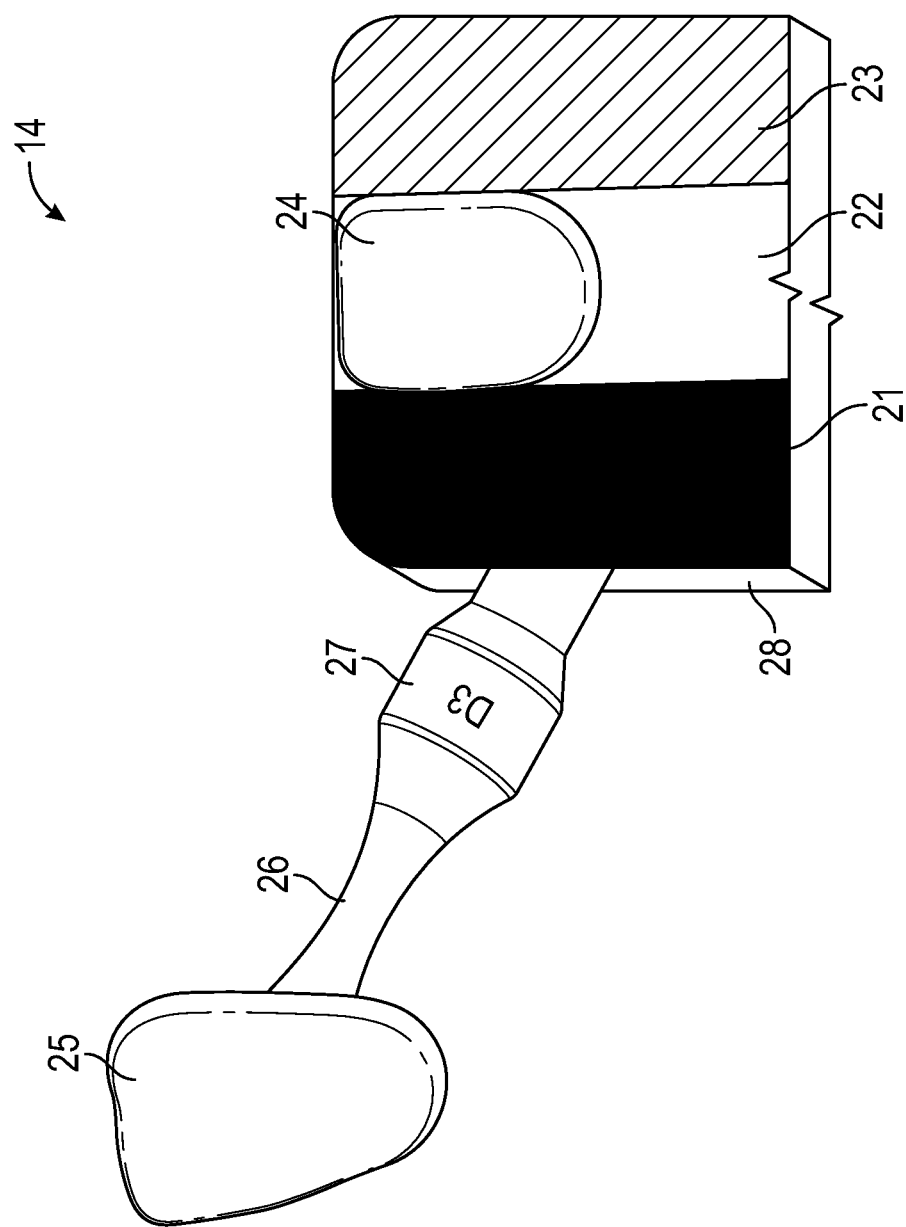
FIG. 2 is a drawing depicting the reference target with shade tabs.

As shown in FIG. 2, the reference target 14 comprises a black reference 21, a white reference 22, a gray reference 23, a first color reference 24 in the form of a shade tab, and a second color reference 25 in the form of second shade tab. The first and second color references constitute different RGB triplets in which at least two of the values are unequal. Preferably, both the first and second color references will have shades that are somewhat similar to the subject to be matched. For example, in the context of tooth shade matching, the first and second color references would constitute shade tabs. In this context, the RGB triplet values of the first and second color references will preferably fall within the following ranges: R: 225-250, G: 175-250, B: 75-235. However, color references with other RGB triplet values can be effective depending on the subject matter, particularly if the RGB triplet values fall within ±50 of the dominant RGB triplet of the subject to be matched.

In the preferred embodiment, the black tab 21, white tab 22, gray tab 23, a first reference shade tab 24 are mounted on a panel 28. The second reference shade tab 25 is mounted on a strip 26 that can be inserted into a groove (not shown) in the panel 28 where it is held by a moderate friction fit which enables the user to adjust the position of the second reference shade tab 25 relative to the panel 28. The ability to adjust position is a beneficial feature with respect to providing flexibility to optimize lighting and location relative to the tooth for which the restoration will be based. The strip 26 may be stamped with the name 27 of the second reference shade tab 25. It is recommended that a reference image be made of the reference target 14 with the name 27 of the second reference shade tab 25 so that a visual reference is created to enable the technician to verify the identity of the second reference shade tab 25. The first reference shade tab 24 may be one of the standard commercially-available shade tabs such as the VITA™ A3. The second reference shade 25 preferably has distinctly different shade than the first reference shade tab 24. For example, if the first reference shade tab 24 is a VITA™ A3, the second reference shade tab could be a VITA™ D3.

Figure 3:
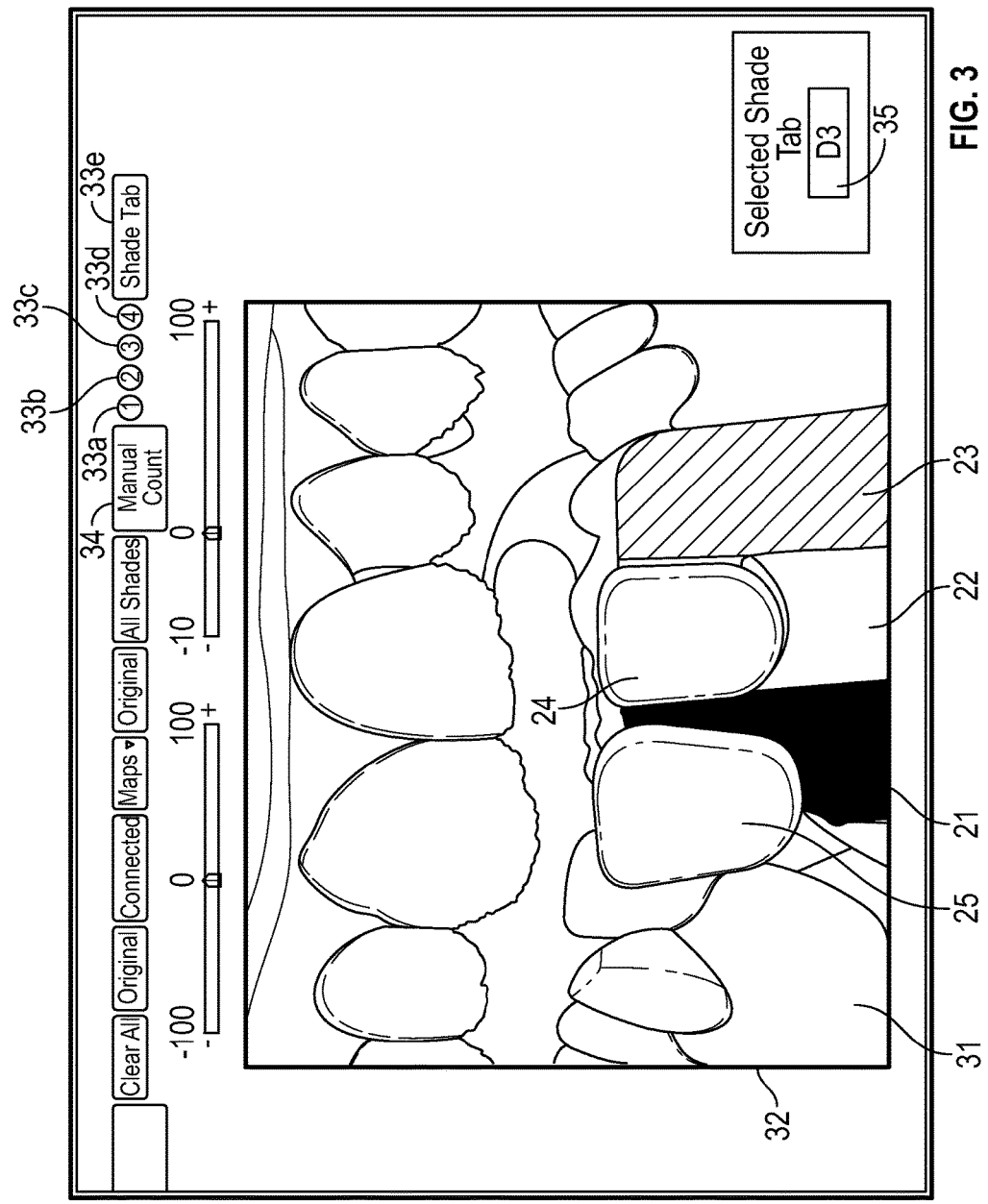
FIG. 3 is a drawing of a computer screen showing the color correction buttons and displaying an image of a mouth with reference target.

When taking the images, the camera should preferably be placed as normal as possible to the tooth being photographed. It is further recommended that several photographs be taken to ensure that the technician will have an adequate image to work from. The image is then transferred into a computer system, via the internet, for color correction and other manipulation. Once the image is loaded into the system, for example by the dentist through the internet, they select the laboratory, giving permission and instant access to the case. The technician may select the desired image to be processed. As shown in FIG. 3, analysis of the image 31 begins by selecting it for display in an image window 32 within the computer screen. A set of color correction buttons 33*a-e* is visible adjacent to the image window 32.

The process is initiated by sequentially selecting points on the reference tabs 21, 23, 23, 24, and 25 by moving a cursor over a point on each reference tab and executing an entry command (e.g., moving the cursor to the desired location and clicking a mouse). The sequence of color correction commands is followed in an order set by the system. For example, in the embodiment shown in FIG. 3, the sequence of selection is white tab 22, black tab 21, the standard shade tab 24, gray tab 23, and selected shade tab 25. The system is configured so that when a reference tab is clicked on, it leaves a red "X" showing the placement of the "click" and it automatically advances to the next selection. To start the process, the user clicks on the #1, white (icon) button 33*a*. Instructions appear telling the user to select the "white tab." After that occurs, the black button 33*b* lights up with associated instructions. The same process happens for the standard shade tab and gray tab. The next mouse command is on the selected shade tab 25 (i.e., normally the shade tab selected by the treating dentist). The name of the shade tab 25 is entered into the shade tab entry window 35. Color correction is implemented by the system when the manual correct button 34 is selected. The software adjusts the red, green, and blue values for each pixel based on a protocol such as gamma correction, gamma followed by linear correction, or splines. The color correction algorithm takes the sampled data from references in the input image and processes it in relation to the known color of references.

In the preferred embodiment, three color correction curves are constructed from the color pairs, one for each of the RGB color channels (red, green, blue). E.g., a correction curve for the red channel is computed so that a spline is constructed from red components of RGB color pairs. The spline is computed so that sampled colors are on the x-axis and reference colors are on the y-axis. All x values that are lower than minimum x value are mapped to minimum y value, and x values that are higher than maximum x value are mapped to maximum y-value. Note that minimum x value corresponds to minimum sampled color value while minimum y value corresponds to minimum reference color value (for each of RGB color components separately). Next, these correction curves are applied to the corresponding RGB channels of the input image in order to get the color corrected image. For example, let some pixel in the input image have RGB value of (235, 232, 200). To correct its red component using the constructed color curves, we search for y value that corresponds to pixel's red component, i.e., x=235. If the associated y value is 246, this pixel will have red component equal to 246 in the output image. We use the same procedure for green and blue color components. Color correction may be accelerated by computing a lookup table based on the correction curves. The goal of the color correction algorithm is to process colors of the input image so that colors of the sampled regions in the image match as closely as possible to the reference colors.

A particularly difficult problem in matching dental restorations is to fabricate a restoration that conceals the color of the stump (the portion of a tooth that has been cut down to receive a crown). When the stump shade is dark, it can adversely affect the appearance of the restoration due to optical effects associated with translucency. The system overcomes this problem by applying a correction factor that accounts for material translucency and thickness and provides the correct choice of material. One means of developing tables or curves for the correction factor is to create models of a stump, shading them with various known shades of stump paint, covering the model stumps with translucent crowns of known shades, and making digital images of the combinations. Once this has been done, the images are analyzed to determine the differential between the nominal and realized color values. The user of the system can activate the feature of applying the color correction factor when evaluating an image of a stump by using the system to determine the shade value of the stump. Once this is done, the system can determine the materials to be used by the technician to prepare a restoration that has an acceptable appearance following installation over the stump.

The system can show multiple combination of maps. For example, shade, translucency, corrected picture or another sequence being shade, corrected picture and modifiers. The system determines the translucency values of the tooth that provides extremely useful information to the technician. The translucency values serves as surrogates to indicate the translucent properties of a tooth. One means of determining the translucency values is to photograph the incisal edges of porcelain shade tabs in a progressively darker sequence against a gray background. Because porcelain shade tabs exhibit some translucent properties, they are not monochromatic. It has been discovered by the inventors that the use of values derived from the incisal edges of shade tabs have particular utility in color matching of dental restorations. Once the images are taken, ranges of translucency values are established to provide areas of extra light, light, medium, and dark translucency values for the purpose of mapping these ranges in an image.

The system can also determine gray-scale values of the tooth. Each pixel in the image is described by a triplet (R, G, B) of intensities for red, green, and blue and the desired number of pixels representing a portion of the tooth are selected using an area cursor. The area cursor may be resized and moved in accordance with user preferences and the size of the image. Once the pixels are selected, the gray-scale value of each pixel is determined by application of an algorithm. Examples of suitable algorithms include the lightness method which averages the most prominent and least prominent colors, i.e., $(\max(R, G, B) + \min(R, G, B))/2$;

the average method which simply averages the values, i.e., (R+G+B)/3; and the luminosity method which calculates a weighted average to account for human perception, e.g., 0.21 R+0.72 G+0.07 B.

In the preferred embodiment, the gray scale value is outputted in the form of a shade tab reference (e.g., VITA™ D2) that shares the same gray scale value. Although the shade tab reference may not reflect the shade of the subject tooth, technicians sometimes find it more useful to begin the manufacture of a restorative work by starting with material that has the same gray scale value as the original tooth and changing the color as opposed to starting with the same shade value and increasing or decreasing the lightness or darkness of the restorative work. It is noted that the technician may perform the value determination prior to color correction if desired.

Figure 4:
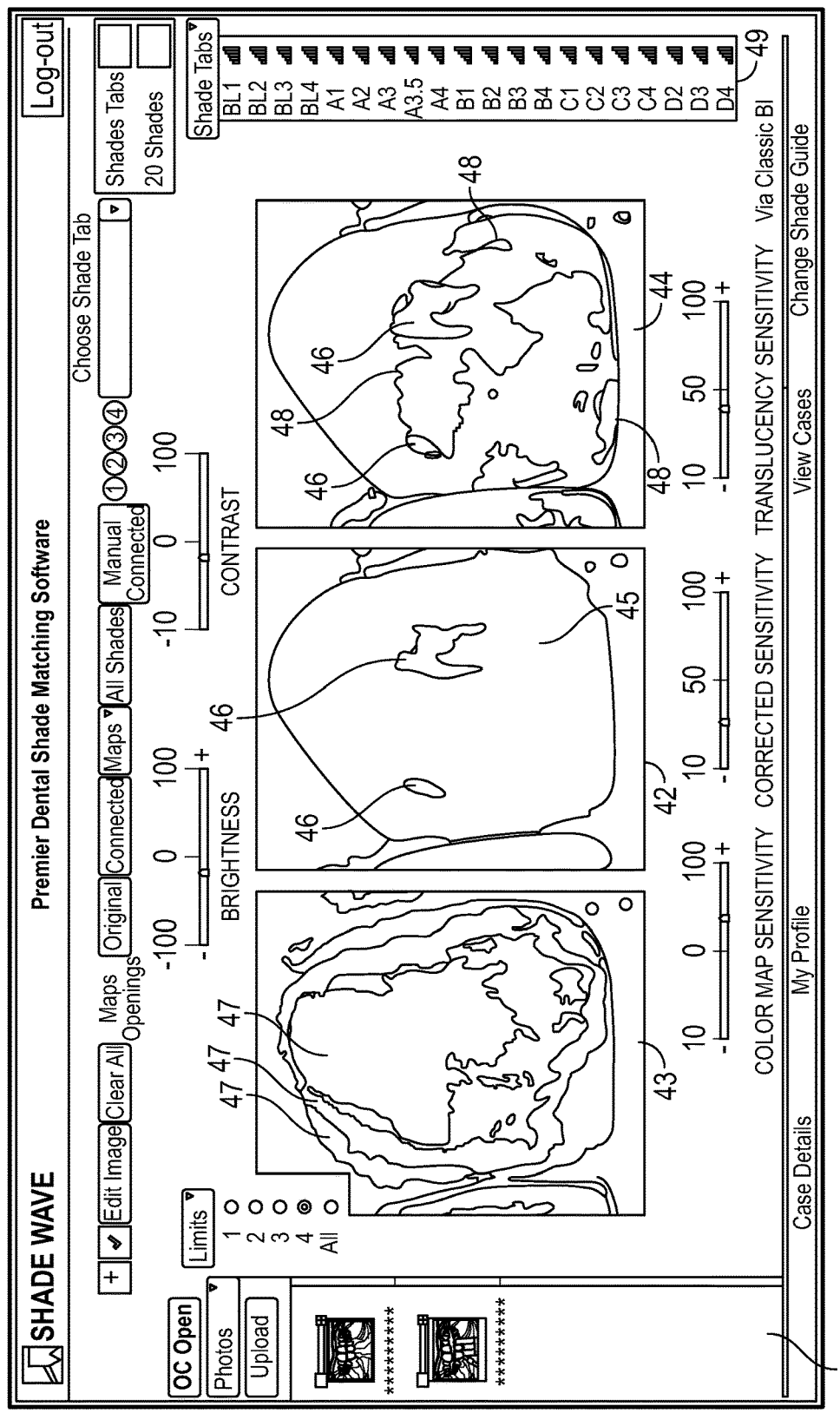
FIG. 4 is a drawing of a computer screen showing an image of the tooth, an image with shade mapping, and an image with value mapping.

As shown in FIG. 4, the results of the color correction and the translucency value determinations are graphically displayed on a screen view 41 that shows the color corrected image 42 of the tooth 45, an image 43 showing the spatial distribution of the shades, and an image 44 showing the spatial distribution of translucency values. The system applies a segmentation algorithm that sort the pixel values into ranges that reflect both reference shade tab values and translucency values of extra-light, light, medium, and dark. The algorithm can also be used to detect blown highlights 46 in which the pixel values are clipped due to an overexposed area of the image and sort them according to a predetermined range. The results of the sorting according to shade tab value are depicted in image 43 and shown in terms of contours 47 that reflect different shade values. Similarly, the results of the sorting according to translucency value are depicted in image 44 and shown in terms of contours 48 that reflect different translucency values. In the preferred embodiment, the blown highlights 46 are depicted as pure white to indicate to the technician the locations of unknown values in order to alert the technician to use judgment when relying on the depiction. Alternatively, the gray scale values can be presented in image 44 instead of the translucency values in a manner analogous to the one described for translucency values.

The goal of the segmentation process is to detect regions on the image colors of which match to one of standard shade tab colors. In addition to color-corrected image, the algorithm has two input parameters that affect the outcome: (1) sensitivity, which controls how sensitive is the algorithm when the matching of input colors with shade tab colors is done and (2) maximum colors limit, which is the maximum number of colors from a shade guide to be used for segmentation. At the first step of the algorithm, Gaussian blur is applied to the image. This helps to get smooth regions at the end. The second step is to go through all pixels of input image and check if a pixel's color matches any shade tab's color. This is done by computing the distance in RGB color space between the color of a pixel and colors of all the shade tabs. The smallest distance is then checked against maximum allowed distance value that is based on the inverse of sensitivity parameter. If the distance is less than this maximum allowed distance, the match is considered found. The match is a shade tab color with the smallest color distance from the input pixel. This procedure is repeated for all pixels. The third step is to compute how many matches each shade tab's color has in the input image. Shade tab colors are then sorted by number of matches in descending order. First N shade tab colors are saved, and the other colors are discarded. Value N is defined by "maximum colors limit" parameter. Having updated the list of shade tab colors, with removed colors that did not pass filtering on previous step, the color matching is performed again as described in the second step. Output of this color matching is now different since another set of shade tab colors (a shorter one) is used. The next step is to group matches on the image that correspond to one shade tab color into regions of pixels. Small regions are removed (absorbed by larger regions) to avoid having too many tiny segments on the segmentation map. Computed regions are then used by the system to generate and display color map and outline map.

Figure 5A:
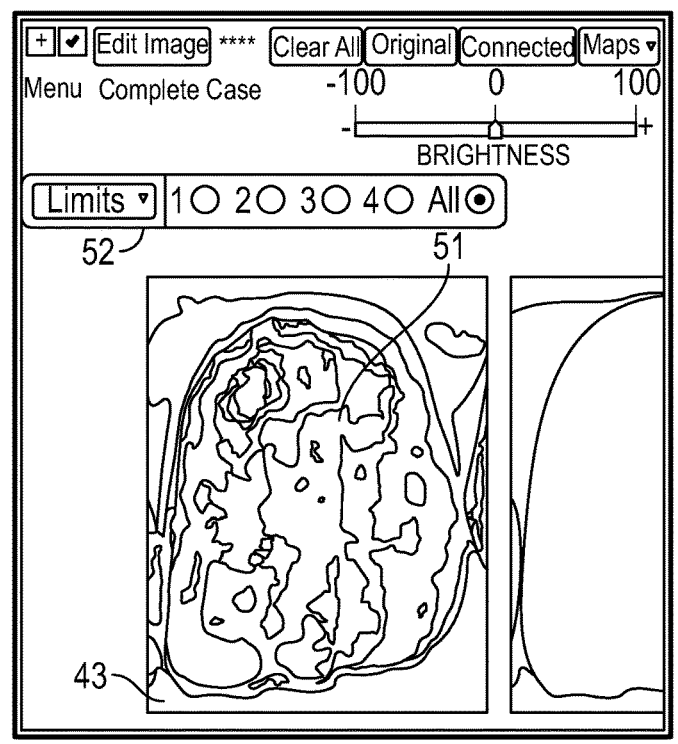
FIG. 5A is a drawing showing the effect of filtering when set to display the full number of shades in an image with shade mapping.
Figure 5B:
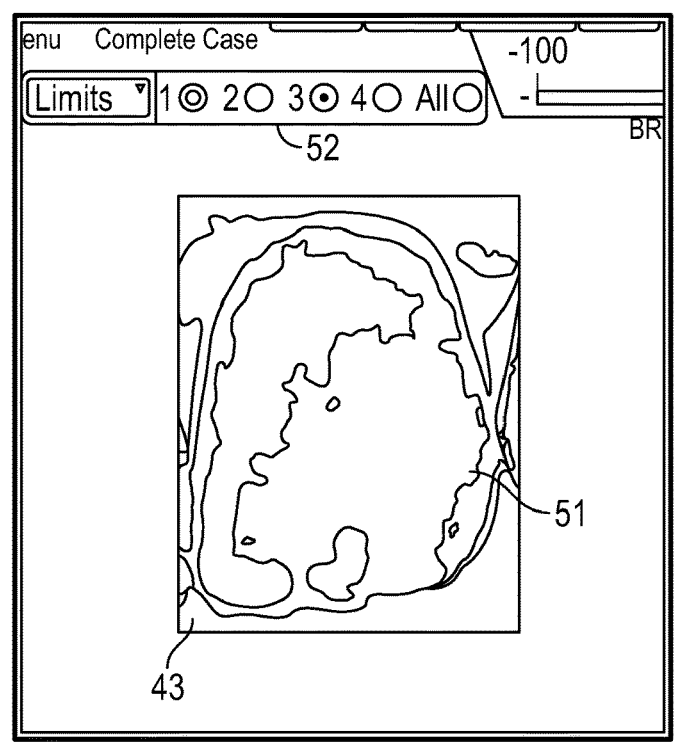
FIG. 5B is a drawing showing the effect of filtering when set to display three shades in an image with shade mapping.
Figure 5C:
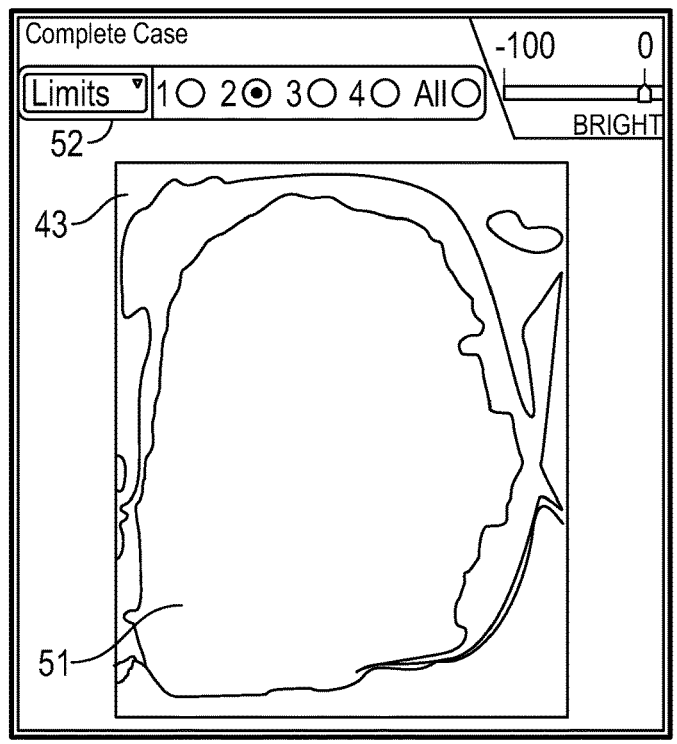
FIG. 5C is a drawing showing the effect of filtering when set to display two shades in an image with shade mapping.
Figure 5D:
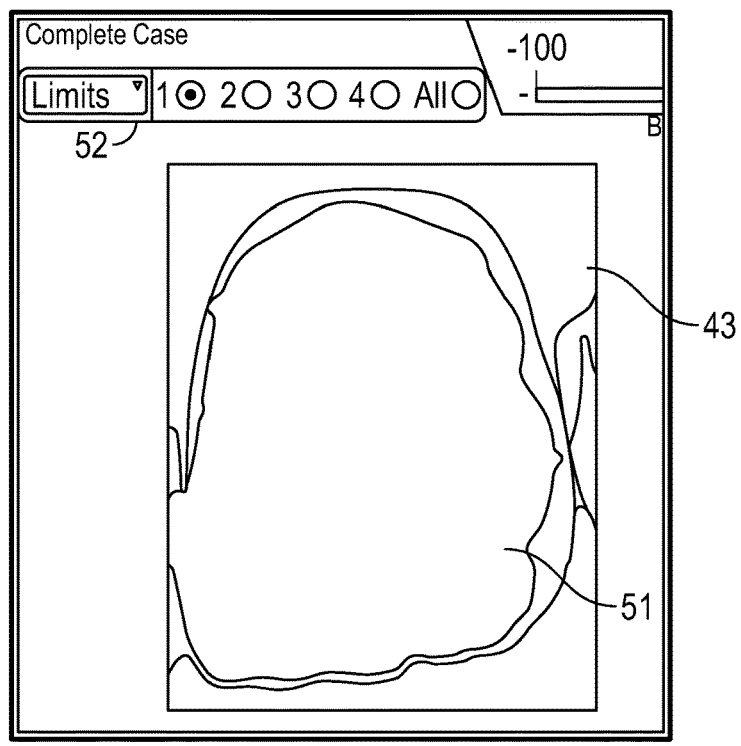
FIG. 5D is a drawing showing the effect of filtering when set to display one shade in an image with shade mapping.

Teeth can have several shades of color as shown in image 43 in FIG. 5A, which depicts the spatial distribution of seven shade tab values on a tooth 51. Such depictions can be problematic for certain kinds of restorations because the abundance of visual information adds to the difficulty and cost of fabricating the restoration. The system thus permits the user to control the number of shades depicted on the tooth by instructing the system via a command box 52 to use segmentation algorithms in which the pixel values are sorted in accordance with a wider set of ranges to prepare diagrams that depict a more limited number of shade or grayscale values in images. For example, the user can specify that the system calculates the ranges and shows the spatial distribution in terms of three shades, as shown in FIG. 5B, two shades as shown in FIG. 5C, or a single shade as shown in FIG. 5D. This simplifies the amount of information provided to the technician and thus facilitates applying technical judgment to reach an acceptable result depending on the circumstances. For example, it may be aesthetically and economically reasonable to construct a restoration for a back tooth that uses a smaller number of shades that would not be appropriate for a front tooth.

The system can store several sets of ranges and thus allow the user to specify different standardized shade guide systems such as those generally offered under the trade names of VITA™, TRUMATCH™, CHROMASCOPE™, and GRANDIO™. The user may select a particular shade guide system at any time by clicking on the appropriate button in the shade selection box 49 shown in FIG. 4 to make the appropriate selection. In addition, the system can allow for the user to install custom sets of shade values. By instructing the system to change shade guides, the pixels are resorted into a different set of ranges. Thus, a user can instantly translate the images from one shade guide system into another.

Figure 6A:
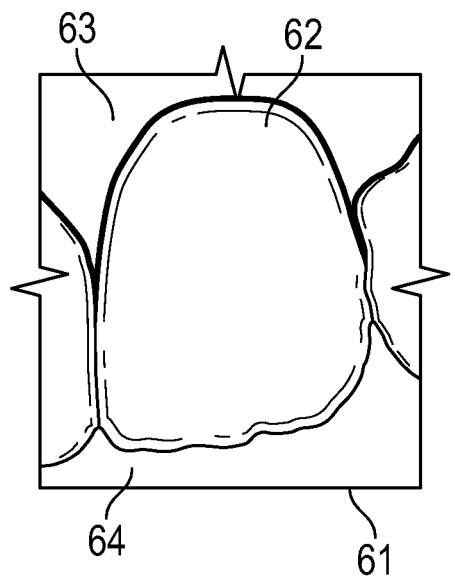
FIG. 6A is a drawing showing the image without application of the masking function.
Figure 6B:
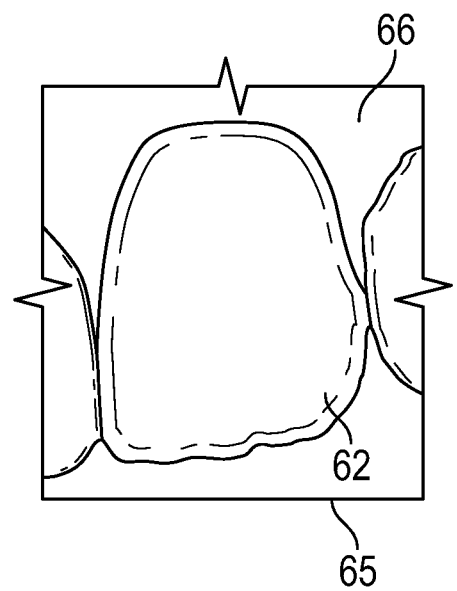
FIG. 6B is a drawing showing the image with application of the masking function.

One difficulty faced by technicians and is that the color of objects surrounding a tooth, such as gum tissue, can interfere with the accurate perception of tooth color. This can result in the selection of the wrong porcelain or stain. As shown in FIG. 6, a typical image 61 of a tooth 62 will show the tooth, gum tissue 63, and empty space 64 surrounding the tooth 61. In a color-corrected image, the gum tissue 63 will typically be pink and the space 64 surrounding the tooth 61 may appear in various colors including black, brown, or pink. If the image 61 was taken under certain conditions or camera settings, the space 64 may display the presence of noise which presents itself as specks of various colors randomly dispersed throughout the space. By instructing the system to execute image segmentation and flood fill algorithms, the system can effect a conversion of image 61 to a masked image in which the tooth is isolated and a mask area 66 replaces the depiction of the gum tissue 63 and empty space 64 that appear in the typical image 61. The user may select the mask area 66 to be of any color, although in general a neutral gray is believed to be the best choice in the majority of cases.

Figure 7:
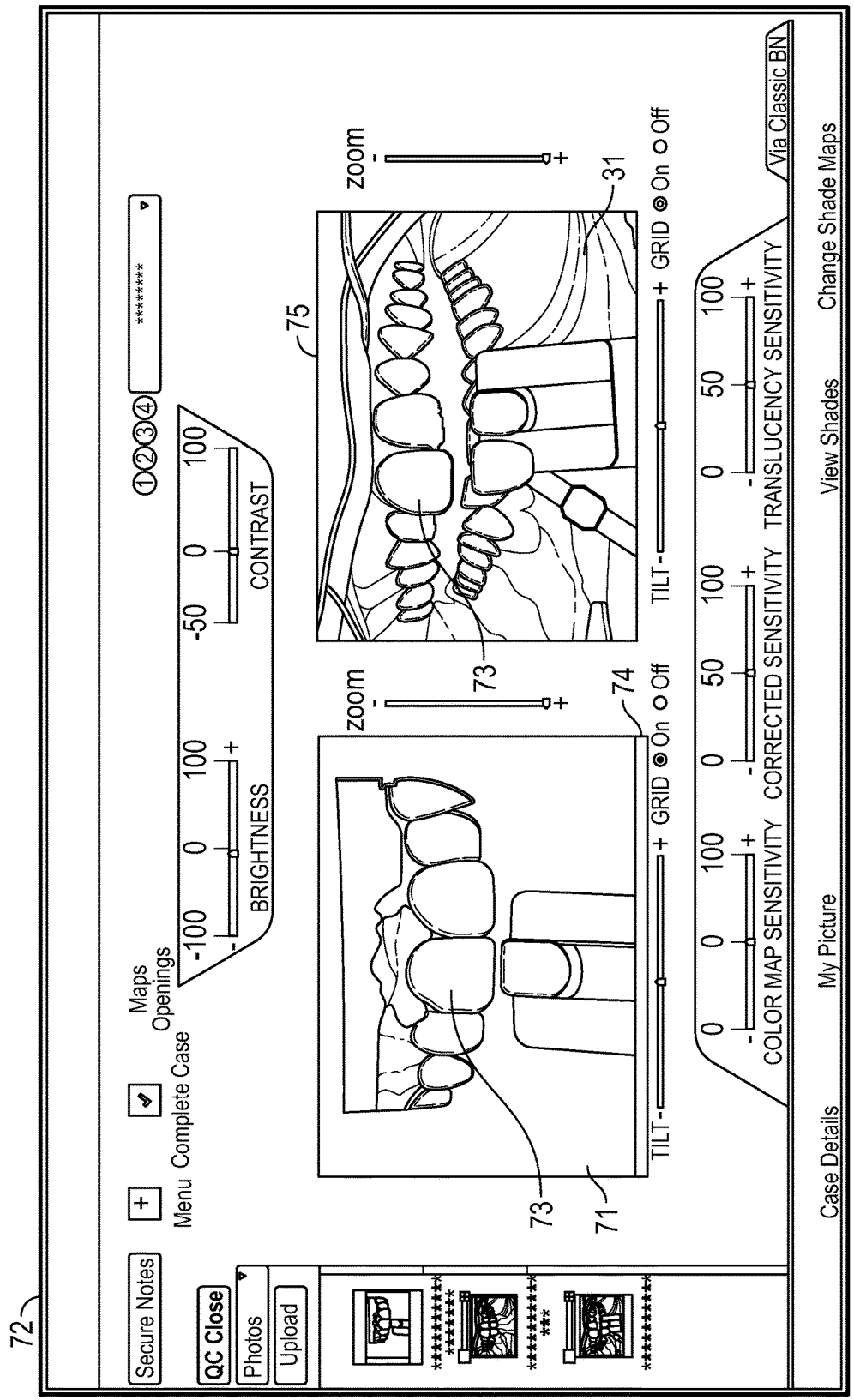
FIG. 7 is a drawing showing the virtual try in feature.

Another means of permitting the technician and dentist to evaluate the quality of the restoration, is to conduct a virtual try-in by virtually fitting an image of the restoration where the prepped or missing tooth would go in the mouth. This is done by taking a digital image of the restoration, preferably using the assembly shown in FIG. 1, loading the image into the computer system, and color correcting it in accordance with the steps associated with FIG. 3. As shown in FIG. 7, the color corrected image 71 of the restoration is displayed next to the color-corrected original image 31 of the patient's mouth on a computer screen 72. The technician can then select the restoration element 73 and drag and drop it from its window 74 over to the other window 75, where it can be placed in a desired position so that the technician may evaluate how well it appears in the mouth. The original image 31 depicting the restoration 73 can be saved as a new image to forward to the treating dentist or patient for input or approval. In addition to the restoration, the technician can perform an additional check by using a representation of shade tab instead of the restoration. In this mode, a virtual try-in may be done either by dragging and dropping a virtual shade tab to the position of the original tooth or by substituting the image content of the restoration 73 with the color information associated with a particular shade tab. The image may also be saved as a new image to compare to the image showing the restoration 73. Comparing an image of a virtual try-in of a restoration with an image of a virtual try-in of a shade tab, allows the technician to detect subtle discrepancies in shape, characterization, shade, reflective line angles, value and or translucency. These are aspects that can detract from a restoration that is otherwise harmonious with respect to hue and chroma.

Although the thrust of the this invention is directed to the application of color matching in the context of dental restorations, it could be adapted to be used in other applications in which color matching is required. In particular, the system is useful for those applications in which the element to be matched has different optical properties than the matching material or in which the element to be matched is located in an environment that can impede the ability to obtain an accurate match. This includes but is not limited to wall paint, dermatology, artificial skin prostheses, and textiles. In such contexts, the color references used in combination with the black, white, and gray points could be something other than shade tabs. In particular, the color references could be selected to be in the approximate range of shade and color of the object to which color matching is desired.

Those of ordinary skill in the art will recognize that the foregoing descriptions cover certain preferred embodiments of the invention. Various modifications can be made to the particular embodiments described without departing from the spirit and scope of the invention.

The invention claimed is:

1. A computer-implemented method of matching the color and appearance of an object in an environmental setting comprising:
   (a) acquiring a first image data file of a scene having a subject color and at least five predetermined references comprising black reference, white reference, gray reference, a first color reference, and a second color reference, of which the first color reference and the second color reference have different RGB triplet values but in which the RGB triplet values fall within ±50 units of the dominant RGB triplet of the subject color;
   (b) loading the first image data file into computer memory;
   (c) color correcting the first image data file to produce a second image data file via an algorithm that utilizes color pairs derived from the predetermined references; and
   (d) displaying the second image file.

2. The method of claim 1 comprising the additional steps of: (e) selecting an area within the second image data file containing pixel values to be recalculated; (f) producing a third image data file by applying a segmentation algorithm to assign each pixel value within the selected area a new pixel value according to a predetermined user-specified number of ranges that reflect predetermined color values; and (g) displaying the third image data file.

3. A computer-implemented method of matching the color and appearance of a tooth comprising: (a) acquiring a first image data file of a tooth and at least five predetermined references comprising a black reference, a white reference, a gray reference, a first shade tab, and a second shade tab, of which the first shade tab and the second shade tab have different RGB triplet values; (b) loading the first image data file into computer memory; (c) color correcting the first image data file to produce a second image data file via an algorithm that utilizes color pairs derived from the predetermined references, (d) selecting an area within the second image data file containing pixel values to be sorted; (e) producing a third image data file by applying a segmentation algorithm to assign each pixel value within the selected area a new pixel value according to a predetermined user-specified number of ranges that reflect predetermined color values; and (f) displaying the third image data file.

4. The method of claim 3 in which the predetermined ranges of step e are based on the colors of shade tabs.

5. The method of claim 3 in which step d further comprises a substep in which the pixels are converted to grayscale values and in which the predetermined ranges of step e are based on the grayscale values of shade tabs.

6. The method of claim 3 in which the predetermined ranges of step e are based on translucency values that have been determined by applying correction factors that are based on the shade value of a stump.

7. The method of claim 3 in which the predetermined ranges of step e are based on the colors of shade tabs and further comprising the additional steps of: (g) producing a fourth image data file by applying a segmentation algorithm to assign a new pixel value to each pixel value within the area selected in step d according to a predetermined user-specified number of ranges that are based on translucency values that have been determined by applying correction factors that account for material translucency and thickness; and (h) displaying the fourth image data file adjacent to the third image file.

8. The method of claim 3 further comprising a step in which the third image file may be selectively modified to leave the selected part of the image visible and to fill in the background surrounding the selected area with a preselected color.

9. The method of claim 3 further comprising the steps of:
   (g) acquiring a first try-in image data file of a dental restoration and at least the five predetermined references comprising a black reference, a white reference, a gray reference, a first shade tab, and a second shade tab;
   (h loading the first try-in image data file into computer memory;

(i) color correcting the first try-in image data file to produce a second try-in image data file via the algorithm that utilizes color pairs derived from the predetermined references;

(j) displaying the second try-in image data file; and (j) selecting the portion of the displayed second try-in image data file that represents the dental restoration and dragging and dropping it to a selected position within the displayed second image file.

10. The method of claim 3 further comprising the steps of:

(g) creating a library of sets of shade guides and modifiers by storing RGB triplet values associated with shade guides and modifiers into computer memory;

(h) using conversion algorithms to translate from one set of shade guides or modifiers to another set.

11. The method of claim 3 in which the predetermined ranges of step e are based on the colors of shade tabs and the first and second color references fall within the ranges of R: 225-250, G: 175-250, B: 75-235; and further comprising the additional steps of:

(g) producing a fourth image data file by applying a segmentation algorithm to assign a new pixel value to each pixel value within the area selected in step d according to a set of predetermined ranges that are based on translucency values;

(h) displaying the fourth image data file;

(i) selectively and reversibly modifying the third image to leave the selected part of the image visible and to fill in the background surrounding the selected area with a preselected color;

(j) selectively and reversibly modifying the fourth image to leave the selected part of the image visible and to fill in the background surrounding the selected area with a preselected color;

(k) acquiring a first try-in image data file of a dental restoration and at least the five predetermined references comprising a black reference, a white reference, a gray reference, a first shade tab, and a second shade tab;

(l) loading the first try-in image data file into computer memory;

(m) color correcting the first try-in image data file to produce a second try-in image data file via the algorithm that utilizes color pairs derived from the predetermined references;

(n) displaying the second try-in image data file; and (o) selecting the portion of the displayed second try-in image data file that represents the dental restoration and dragging and dropping it to a selected position within the displayed thrid image file.

12. A color matching device comprising a non-transitory computer-readable medium having stored thereon a set of instructions, executable by a processor, the instructions including: a set of instructions which, when loaded into a memory and executed by the processor, causes the acquisition of a first image comprising an object to be color matched, said image further comprising a black tab, white tab, gray tab, a first reference shade tab, and a second reference shade tab; a set of instructions which, when loaded into a memory and executed by the processor, causes to create a second image by color correcting the first image in accordance with inputs associated with each of said tabs; and a set of instructions which, when loaded into a memory and executed by the processor; causes to create a third image based on the second image in which a defined set of colors in a selected part of the image are mapped according to a predetermined user-specified number of ranges that reflect predetermined color values.

13. The device of claim 12 further comprising a set of instructions which, when loaded into a memory and executed by the processor; causes to create a fourth image based on the second image in which the transparency values of a selected part of the image are mapped in accordance with a set of preselected ranges of transparency values that have been determined by applying correction factors that are based on the shade value of a stump.

14. The device of claim 12 further comprising a set of instructions which, when loaded into a memory and executed by the processor; causes to create a fourth image based on the second image in which the grayscale values of a selected part of the image are mapped in accordance with a set of preselected ranges of grayscale values.

15. The device of claim 12 further comprising a set of instructions which, when loaded into a memory and executed by the processor; causes to create a masked image in which the selected part of the image is visible and the remaining background is filled with a preselected color.

16. The device of claim 12 further comprising a set of instructions which, when loaded into a memory and executed by the processor, causes the acquisition of a try-in image comprising a dental restoration and further comprising the black tab, the white tab, the gray tab, the first reference shade tab, and the second reference shade tab;

a set of instructions which, when loaded into a memory and executed by the processor, causes to create a second try-in image by color correcting the first try-in image in accordance with inputs associated with each of said tabs; and a set of instructions which, when loaded into a memory and executed by the processor, causes to select the portion of the second try-in image data file that represents the dental restoration and to drag and drop it to a selected position within the second image file.

17. The device of claim 12 further comprising an assembly for the acquisition of the first image comprising an adjustable extension arm that supports a camera at the proximal end and supports a reference target at the distal end and at a predetermined distance and angle, said reference target further comprising the black tab, the white tab, the gray tab, the first reference shade tab, and the second reference shade tab.

18. The device of claim 12 further comprising a set of instructions which, when loaded into a memory and executed by the processor, causes to translate from one set of shade guides or modifiers to another set.

19. The device of claim 12 further comprising a set of instructions which, when loaded into a memory and executed by the processor; causes to create a fourth image based on the second image in which the transparency values of a selected part of the image are mapped in accordance with a set of preselected ranges of transparency values;

a set of instructions which, when loaded into a memory and executed by the processor, causes the acquisition of a try-in image comprising a dental restoration and further comprising the black tab, the white tab, the gray tab, the first reference shade tab, and the second reference shade tab;

a set of instructions which, when loaded into a memory and executed by the processor, causes to create a second try-in image by color correcting the first try-in image in accordance with inputs associated with each of said tabs; and a set of instructions which, when loaded into a memory and executed by the processor, causes to select the portion of the second try-in image data file that represents the dental restoration and to drag and drop it to a selected position within the second image file.

\* \* \* \* \*